(12) United States Patent
Fujita

(10) Patent No.: US 6,386,868 B1
(45) Date of Patent: May 14, 2002

(54) DENTAL ARTICULATOR AND ITS TRANSFORM PLATE

(76) Inventor: Kazuya Fujita, 14-18, Nihominami 2-chome, Minami-ku, Hiroshima-shi, Hiroshima 734-0027 (JP)

( * ) Notice: Subject to any disclaimer, the term of this patent is extended or adjusted under 35 U.S.C. 154(b) by 0 days.

(21) Appl. No.: 09/762,675
(22) PCT Filed: Dec. 28, 1998
(86) PCT No.: PCT/JP98/06013
 § 371 Date: Feb. 12, 2001
 § 102(e) Date: Feb. 12, 2001
(87) PCT Pub. No.: WO00/21457
 PCT Pub. Date: Apr. 20, 2000

(30) Foreign Application Priority Data

Oct. 15, 1998 (JP) .......................................... 10-293609

(51) Int. Cl.[7] .............................................. A61C 11/00
(52) U.S. Cl. ............................ 433/60; 433/55; 433/56
(58) Field of Search ............................. 433/55, 56, 57, 433/60 OR, 63, 65

(56) References Cited

U.S. PATENT DOCUMENTS

| | | | | |
|---|---|---|---|---|
| 198,853 A | * | 1/1878 | Oehlecker | 433/57 |
| 1,733,507 A | * | 10/1929 | McCollum | 433/56 |
| 3,052,030 A | * | 9/1962 | Spence | 433/56 |
| 4,163,319 A | * | 8/1979 | Ouaknine | 433/60 |
| 4,391,589 A | * | 7/1983 | Monfredo et al. | 433/63 |
| 4,547,154 A | * | 10/1985 | Puschmann | 433/56 |
| 4,687,442 A | * | 8/1987 | Wong | 433/63 |
| 5,267,858 A | * | 12/1993 | Ono | 433/58 |

FOREIGN PATENT DOCUMENTS

| | | | |
|---|---|---|---|
| JP | 2-29245 | * | 1/1990 |
| JP | 4-506616 | * | 11/1992 |
| JP | 6-36812 | * | 9/1994 |
| JP | 7-41452 | * | 9/1995 |

* cited by examiner

*Primary Examiner*—John J. Wilson
(74) *Attorney, Agent, or Firm*—Armstrong, Westerman & Hattori, LLP

(57) ABSTRACT

A dental articulator (5) capable of reproducing or analyzing a physiological occlusion status by implementing a pressure receiving function and a traction function capable of operating in all the motion directions equivalently provided by a jaw joint function of a living body with a teeth plaster model fitted between upper and lower jaw frames, comprising an occlusal plane table (8) having the same anteversion angle as the occlusal plane oblique angle of a living body; a bite analysis plate (9) on which average positions of a spew center (91) and a posterior motion axis (92) are set at a plurality of positions and they are sketched in pairs with the average positions of the spew center on one side and those of the posterior motion axis on the other side of the plate; an incisal guidance plate (56) in which an inverted conical slope for mapping front-and-rear, right-and-left inclinations of the cusp is cut to allow the tip of an incisal guide to slide; and a transform plate (1) which is fitted using a lower jaw frame (52) as a base, wherein the teeth plaster model (7) of a lower jaw is mounted on and fitted to the transform plate (1) to effect a shift operation, thereby reproducing physiological occlusion status in conjunction with an intercuspal position and a posterior occlusion position of a living body.

6 Claims, 14 Drawing Sheets

DENTAL ARTICULATOR AND ITS TRANSFORM PLATE

FIELD OF THE INVENTION

The present invention relates to a dental articulator and a conversion plate therefor which are used by dentists and dental technicians in the clinical field during treatment of the occlusion of upper and lower dentition and during the creation of prosthetics for reproducing and analyzing physiological occlusion states relating to the intercuspal position and the posterior occlusal position, wherein using an occlusal plane table with a forward inclination of 10 degrees, an upper jaw dentition plaster model is mounted onto an upper jaw frame and in parallel with the Camper plane which is a prosthetic plane, a lower dentition plaster model is mounted onto a conversion plate which has been mounted and fixed to a lower jaw frame serving as a base, and the physiological relationship of upper and lower jaws is reproduced so that the upper and lower jaws are brought into the state of centric relation (anterior superior position), and further physiological occlusion states relating to the intercuspal position and to the posterior occlusal position can be reproduced or analyzed by the operation of shifting said conversion plate and adjusting all directions of lower jaw movement.

The physiological occlusion states herein means the intercuspal position—the starting point and stopping point of occlusion, and the posterior occlusal position—the limited position where ligament is tensioned.

In some cases, this conversion plate, if used as an accessory part to be incorporated into an existing articulator which has in advance been disassembled for re-assembly, can be provided as an accessory part for converting the function of said articulator into that of this new articulator for reproducing jaw movement in a person more accurately.

PRIOR ART

Since it is effective to reproduce the intercuspal position and the posterior occlusal position in the field of prosthetic treatment, there have been proposals on simulating these positions in an articulator and other treatment tools. For the prosthetic treatment of partial or full dentures, such instruments are known as an ear-face-bow for reproducing the positional relationship between the upper jaw and the skull, an occlusal plane table for arranging denture detention, a Broadrik's occlusal plane analysis table for arranging the lower jaw occlusal cusp on an arc of 10 cm radius, and Gerber's articulator for reproducing the posterior occlusal position.

For example, the ear face bow is widely employed with the intention of reproducing the Frankfurt plane (FH plane) using the orbitale (Or) and the opening of external auditory meatus (Po). There still remains a problem, however, regarding the precision in the horizontal direction since a rod is inserted into the external auditory meatus of feeble. tissue.

On the other hand, in case of full dentures, the occlusal plane determination method using the Camper plane is highly precise in the horizontal direction and has an advantage that the median line can be determined using an upper jaw occlusion model. In the conventional technique of this method, however, a problem still remains regarding the Balkwill angle on the sagittal plane (sagittal upward direction) since the upper Jaw frame and the occlusal plane table are set to be parallel with each other.

Further, in the Broadrik occlusal plane analysis table for arranging the occlusal cusps of the lower jaw on an arc, there remains a problem that the right and left Spee curves do not match with each other since each Spee center is established separately.

Further, Gerber's articulator, which can reproduce the posterior occlusal position, has a problem in the amount and direction of posterior movement.

That is, in well-known Gerber's articualtor (trade mark: Condylator ), a slide clutch is attached to the area of temporomandibular joint so that the intercuspal position and the posterior occlusal position can be reproduced respectively when the clutch is locked and unlocked. FIG. 15 shows a photograph carried in a catalogue. This type of articulator has not yet widely been used in Japan because of its high cost.

It has been advocated that the jaw oral cavity system in a person not merely conduct the movements relating to the mastication function but also has a function of helping the head balance in the directions of forward, backward, left, and right, that is, for the inertia balance system to determine position and axis of the head in posture control (hereafter referred to as a new guiding principle).

Thus, the occlusion dentition is determined by the activity of the jaw closing muscles with the temporomandibular joint as a fulcrum. In a normal case, the muscle activity during tapping at the intercuspal position maintains balance in the directions of left, right, front, and back, and that stabilized position is anatomically called the stabilized condyle position and is clinically called the centric relation (anterior superior position).

Techniques in the prior art, however, only focus on one element of the mastication function and lack an overall viewpoint. Further, they reveal inconsistency in that different methods are employed for handling jaws with teeth and those without teeth.

Accordingly, a method based on the new guiding principle for diagnosing and treating physiological occlusion becomes important to clinical workers treating patients with temporomandibular arthrosis and creating prosthetics that protect susceptible retrodiscal tissue of the temporomandibular joint.

The inventor has been making some proposals on methods for diagnosing and treating physiological occlusion. Briefly speaking, at the physiological occlusion state, the lower jaw normally has a movement range of about 12 mm for forward and about 1.2 mm ±1.0 mm for backward from the intercuspal position with the teeth closed at the centric relation (anterior superior position). In the forward movement, the incisor area describes a movement curve in a forward and downward direction due to guiding contact between the upper incisors lingual side and the lower incisors labial side, and the condyle area describes a movement curve in a forward and downward direction on a downwardly, convex arc. In the posterior movement, the molar area describes a movement curve in a backward and downward direction due to the guiding contact between the mesial slopes of the lingual cusps of the upper molars and the distal slopes of the buccal cusps of the lower molars, and the condyle area describes a movement curve in a backward and upward direction on an upwardly convex arc [(For example, Fujita Kazuya: Temporomandibular Arthrosis— Criteria on Physiological Occlusion (Dental Booklet Series 35, (Dental Forum, 1997)].

Though a Gerber's Condylator intends to reproduce the intercuspal position and the posterior occlusal position using a clutch at the area of temporomandibular joint, the instrument is unsatisfactory because it fails in representing the accurate behavior of temporomandibular joint. Namely, though it is primarily known that condyle movement is about 0.2 mm to 2.0 mm in its amount and is backward and upward about 20 to 30 degrees with respect to the Frankfurt plane in its direction, Gerber's Condylator moves only in the backward and downward direction and the movement amount is about 0.5 mm.

An articulator commonly used by dentists and dental technicians in Japan (hereafter referred to as a conventional articulator) is not structured to allow the temporomandibular joint area to move backward, that is, since the conventional articulator does not make it possible to reproduce the posterior occlusal position while making it possible to reproduce the intercuspal slope. In addition, the function (clutch) of Gerber's Condylator can hardly be incorporated to use. FIG. 14 shows an example of a conventional articulator. The reference numerals in this drawing do not correspond to those in other attached drawings for the present invention.

In these situations, it is highly expected to develop a new dental articulator based on a new guideline—possessing a bilateral symmetry under the physiological gravity, allowing an occlusal plane to be set to a forward incline of 10 degrees, possessing a Spee curve in harmony with the lower jaw pendular movement in a person, allowing the intercuspal or posterior occlusal position and the balanced cusp slopes toward left, right, front, and back to be reproduced.

One approach in this case would be to improve the conventional articulator having the existing function of Gerber's articulator Condylator (if detailed, an improved function for reproducing jaw movement), that is, adding a part (a converter plate of the present invention) as a new structural element for converting the conventional function into that of a new articulator while taking advantage of the existing articulator's structure. Then, the goal will effectively be achieved by combining various technologies in the prior art (collecting the functions from conventional instruments).

The present invention has been developed in light of these circumstances and intends to resolve the above issues and to provide an embodiment of a new dental articulator based on a new guiding principle. Another object of the invention is to provide a conversion plate for a dental articulator so that jaw movement in a person can be reproduced more accurately by simply operating said plate.

In some cases, this conversion plate is provided as a single part because the plate, if used as a part to be incorporated into a conventional articulator which has in advance been disassembled for re-assembly, can convert the function of said articulator into that of this new articulator.

SUMMARY OF THE INVENTION (DISCLOSURE OF THE INVENTION)

A first aspect of the invention is a dental articulator which actualizes the load receiving function and the tractive function to be operable in all the directions which are equivalent to those in the function of a temporomandibular joint in a person, comprising:

an occlusal plane table formed to have a slant surface with a forward inclination similar to that of an occlusal plane in a person;

an occlusion analysis plate with averaged positions established and drawn at multiple locations for a Spee center and a posterior movement axis which are constitutional elements in a person;

an incisor guiding plate provided with an inverted slant conical surface to map the forward, backward, left, and right intercuspal inclinations for reproducing jaw movements in a person toward forward, backward, left, and right so that the tip of an incisor guiding pin is slid along said slant surface; and a conversion plate mounted to a base of a lower jaw frame together with a lower jaw plaster dentition model for operating and reproducing physiological states for the intercuspal position and the posterior occlusal position in a person.

Thus, the articulator makes it possible to reproduce or analyze the physiological occlusal states.

The articulator herein is preferably provided with a face bow as an accessory part for recording the Camper plane which is parallel to an occlusal plane in a person.

A second aspect of the invention is a conversion plate for a dental articulator which, including a lower jaw frame as a base, is mounted (incorporated) together with a dentition plaster model onto (into) said dental articulator whose condyle path angle has been set to 30 degrees so that physiological occlusion states related to intercuspal position and posterior occlusal position are operated and reproduced by the shift operation, wherein a main body of said conversion plate is divided into an upper structural member and a lower structural member; binding surfaces of both members are formed to rise and fall so that the surfaces can be fitted or engaged with each other by male and female elements and can slide in the direction parallel with the Condyle path angle; both said members are provided on the left and right side faces thereof with either a threaded hole or an oblong hole for a temporary fixing by a screw; and said upper structural member with said lower jaw dentition plaster model mounted is slid on said binding surfaces.

Here, said male and female elements are a recess and a protuberance, and triangular elements, said binding surfaces fit with each other by means of the recess and projection and engage with each other by the triangular elements, and said binding surface related to said engagement is formed to include the two sides crossing at the right in a right triangle with two interior angles of 30 degrees and 60 degrees other than a right angle so that the inclination in said sliding direction and the condyle path angle are the same. Accordingly, both members have such a binding relationship in which both members can slide (be operated to shift) relatively to each other in a forward and downward direction (backward and upward) of 30 degrees in the mounted elevation view.

Thus an occlusal state is relatively converted between said conversion plate and an upper jaw dentition plaster model mounted onto an upper jaw frame of said dental articulator.

That is, 1̂ not only the occlusal state related to intercuspal position can be operated and reproduced by engaging and fixing the upper structural member and the lower structural member with each other, 2̂ but also the physiological occlusal states related to intercuspal position and posterior occlusal position can be operated and reproduced by sliding the upper structural member and thereafter sliding the lower structural member in a forward and downward direction of 30 degrees and then fixing both members to each other. (The operation procedure is later described.)

DESCRIPTION OF THE MOST PREFERRED EMBODIMENTS OF THE PRESENT INVENTION

Referring to the attached drawings, the present invention will hereafter be described in detail.

Firstly, the "relationship between an articulator and a person" and the "survey on jaw movement in terms of geometric and anatomical viewpoint", based on a new guiding principle, will be summarized.

"The Relationship Between an Articulator and a Person"

Figure 1:
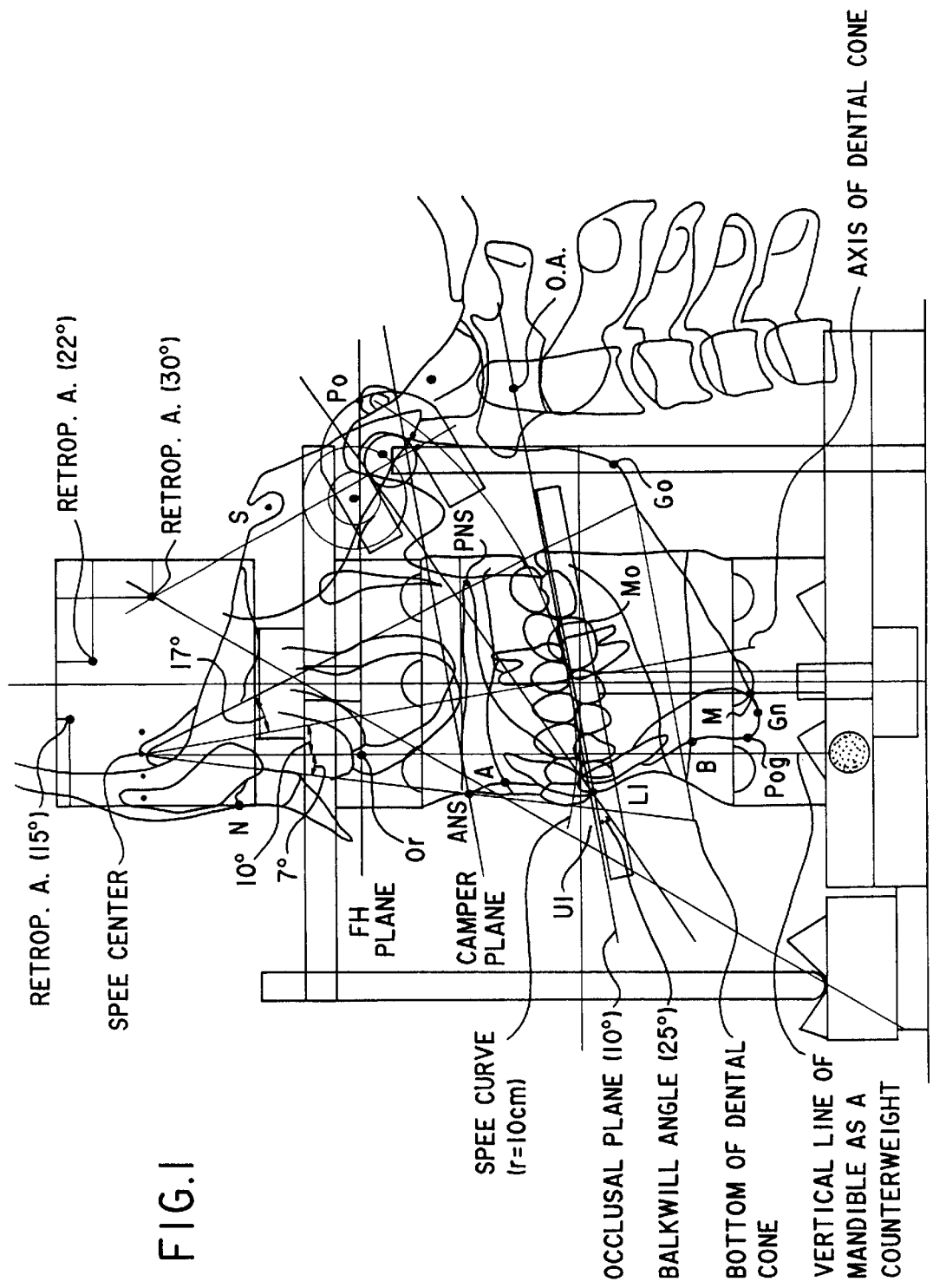
FIG. 1 is a side view showing a relationship between a dental articulator and a person (shown in cephalo)

FIG. 1 shows a relationship between a person (shown in cephalo) and a dental articulator (hereafter referred to as an articulator). The articulator's upper jaw frame and FH plane (Or-Po) are parallel and this relationship is basic throughout the discussion. According to cephalo-analysis, the angle between the occlusal plane (U1-Mo) and the FH plane is about 10 degrees, the Balkwill angle (an angle formed between the occlusal plane and an imaginary line drawn from the center of the condyle's upper surface to the incisor point) is about 25 degrees, the Camper plane (naso-auditory meatus line, prosthetics plane) and occlusal plane are nearly parallel with each other, and the length of each side of the Bonwill triangle is about 10 cm.

"Survey on Jaw Movement in Terms of Geometric and Anatomical Viewpoint"

The inventor performed an analysis using jaw movement data measured through a jaw movement measuring instrument with 6-degrees of freedom and X-ray lateral cephalo photos, and the surveyed result is as follows.

The mandibular condyle makes a pendular movement, at an angular acceleration of about 90 degrees in the forward and downward direction and along a portion of a 12 mm radius arc whose radial center lies at the center of the articular eminence, starting from a point (intercuspal position) about 33 degrees below the Frankfurt plane (horizontal plane). In addition, the direction of the normal (a perpendicular to the tangent) of the condyle ball at the starting point corresponds to the direction of the vector of force applied to the mandibular condyle at the intercuspal position, and this normal passes near the area around the apex (glabella point) of the oral cavity (dental cone). Namely, from the dentistry viewpoint, a curve connecting the buccal cusp of the mandibular molars to the mandibular condyle is known as the Spee curve with a radius of about 10 cm, and the center of the dental cone becomes the stress center for the maxilla and mandible (including the temporomandibular joint) when the jaw is closed at the intercuspal position. [Anatomically, the glabella point lies in the area near the apex of the criatagalli lying in the posterior area of frontal sinus, namely in the anterior area of the frontal sinus.]

According to cephalo-analysis, the angle between the occlusal plane, formed by connecting the midpoint of the upper and lower central incisors to the midpoint of the upper and lower molars, and the FH plane (horizontal plane), is on the average about 10 degrees for adult Japanese (Izuka and Ishikawa, Reference for case analysis method based on X-ray cephalo standard photos—for the group of adult Japaneses with normal occlusion, Journal of Japanese Dentition Correction Academic Association, No.16, 1957). Since the center line through the dental cone is at a right angle with the occlusal plane, the dental cone axis, is angled forward about 10 degrees with respect to the vertical. Since the movement mechanism fundamentally works forward (in the direction of the forehead), a rebound element is necessary for the forward tilt of the upper body.

Figure 2:
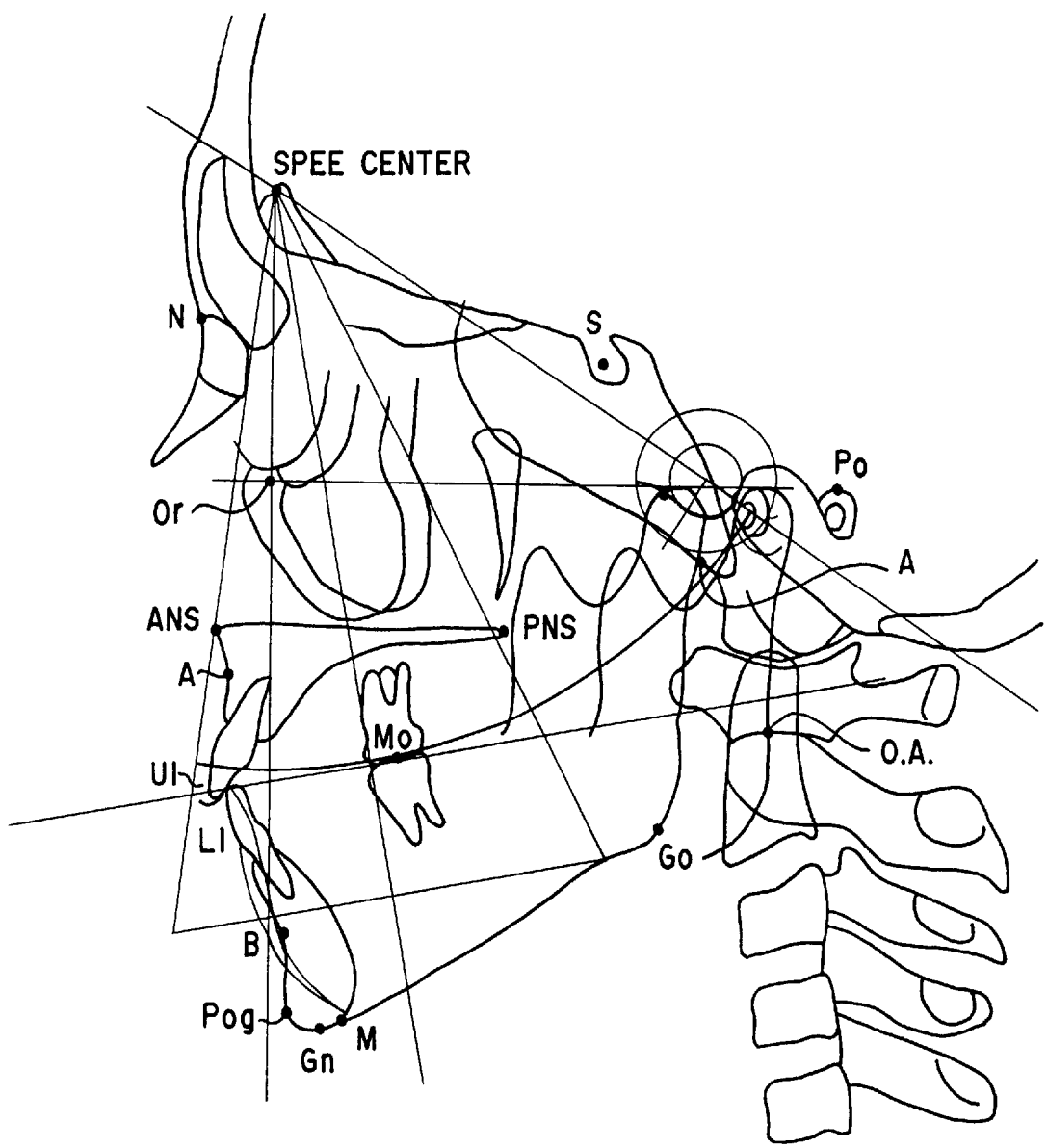
FIG. 2 is a side view of an oral cavity cone at an intercuspal position.

Since the mandible in a person, has a balancing function for the, cranium (pendular movement of the mandible as a counterweight), a detection was performed for the rotational center of the forward and backward movement of the mandible at mandibular resting position (mouth open gap of about 3 mm, mouth open angle of about 2 degrees) when projected onto a sagittal plane, and it turned out that the center lies at the apex of the dental cone which as mentioned is the center of stress, because the mandibular condyle moves forward and downward tangentially to the FH plane (horizontal plane) at about 50 degrees (because of the sagittal projection, the angle of the normal toward the dental cone apex becomes steeper from 33 degrees to about 40 degrees) and the front incisors of the mandible makes a tangential movement forming a right angle to the vertical axis. FIG. 2 shows the dental cone at the intercuspal position.

That is, the swinging movement of the mandible hanging open naturally by the lateral ligaments and the temporal muscle is considered to be a pendular movement of the mandibular serving as a counterweight, with the radial center at the apex of the dental cone.

Thus, since the intercuspal position, which is the final resting point for the maxilla and mandible, can be considered to be a dynamically static point where an infinitesimal amplitude and an infinite frequency are given, it is possible to infer that the line drawn through the buccal cusps of the lower molars, which are the closing point of the mandible, is arranged on an arc or a spherical surface with its center at the focal point of the pendular movement. Accordingly, the pendular movement of the mandibular counterweight which serves as a posture balancing mechanism, and the occlusion, in terms of dentistry, can harmonize with each other.

The movement of the upper vertebrae plays a cooperative role for that of opening and closing the upper and lower jaws. The mouth opening movement of a maxilla model was surveyed, keeping the mandible static. At the intercuspal position, since the normal for the condyle movement passes through the area near the pivot center of the posterior condyle (flexion/extension axis of the atlas occipital joint), the movement between the occipital bone and the 1st cervical vertebra (the atlas occipital joint) has a high degree of freedom. In a condition with the skull tilted back about 5 degrees around the posterior condyle pivot point as a rotation axis and the mouth open about 10 mm, since the normal for the condyle movement passes through the pivot point of the 1st cervical vertebra (the flexion/extension axis of lateral atlanto axis, near the center of the odontoid process, this area corresponds to the pivot center of the median atlanto axis joint which is the pivot joint), the movement between the 1st and 2nd cervical vertebrae (lateral atlanto axis joint) also has a high degree of freedom. Further, in a condition with the 1st cervical vertebra tilted about 5 degrees backward and with the mouth open about 15 mm, since the normal for the condyle movement passes through the pivot point for the 2nd cervical vertebra (vertebral body center of the 3rd cervical vertebra), the movement between the 2nd and 3rd cervical vertebrae (intervertebral disc and intervertebral joint) has a high degree of freedom of movement. In a condition with the 2nd vertebra tilted about 5 degrees and with the mouth open 20 mm, since the normal for the condyle movement is now parallel with a vertical line (with the mandibular condyle hanging straight down by the lateral ligament), the backward rotational movement of vertebrae below the 3rd vertebra have the effect of making the mandibular condyle cross over the articular eminence. Since a plane with a forward inclination of 10 degrees with respect to the FH plane always passes through the rotational center of the first vertebra (near the center of the odontoid process) while the mouth is being closed and opened, it has an important meaning how to establish the occlusal plane.

Figure 3:
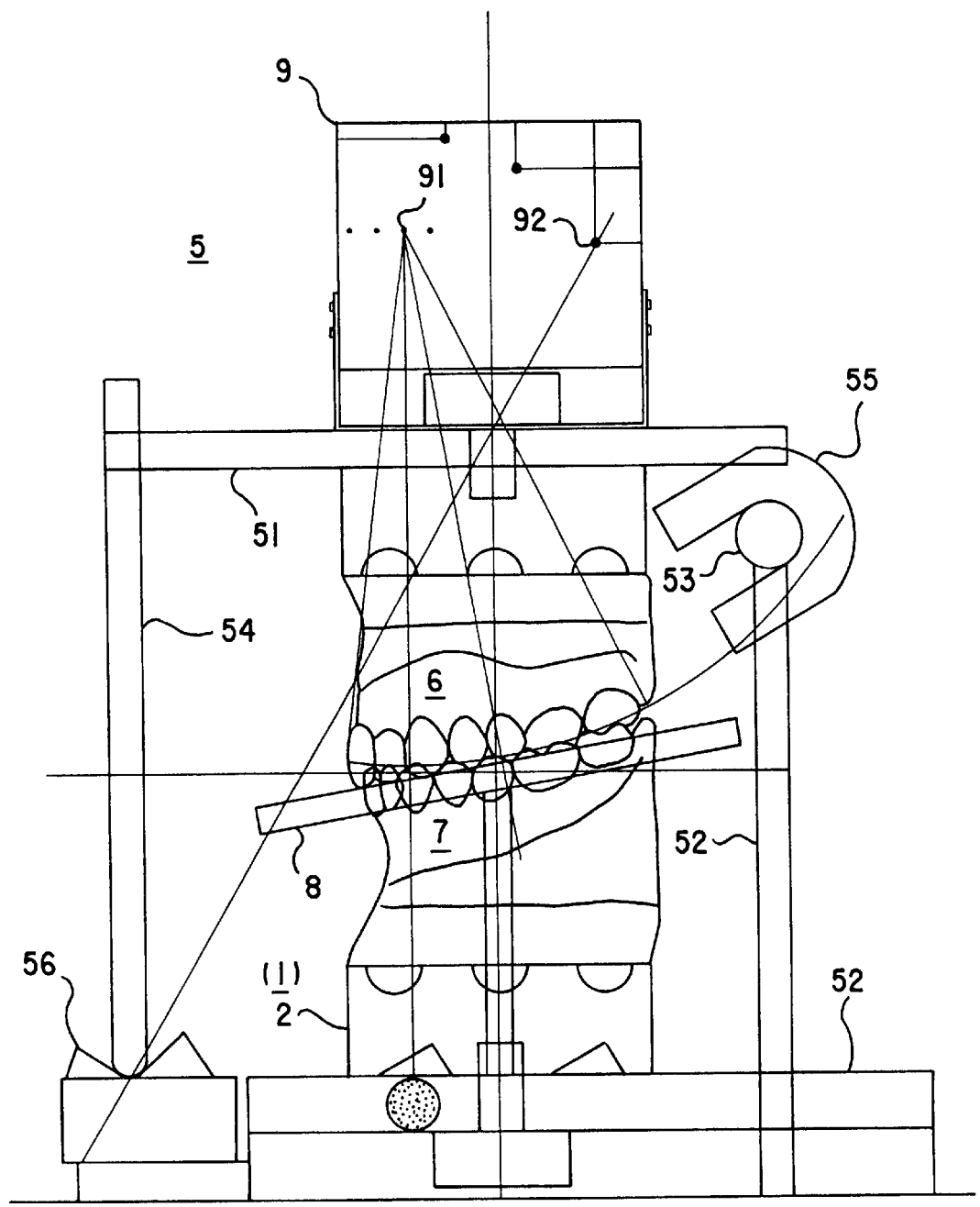
FIG. 3 is a side view showing a structure of a dental articulator.

The articulatory of the present invention takes into account the above knowledge, and thereby makes it possible to reproduce and analyze the states of physiological occlusion by actualizing the load function and tractive function to be operable in all the directions which are equivalent to those in the temporomandibular function in a person. As shown in FIG. 3, a side view of an articulator (5), the articulator is characterized in that said articulator comprises an occlusal plane table (8) formed to have a slant surface with a forward inclination similar to that of an occlusal plane in a person; an occlusion analysis plate (9) with averaged positions established at multiple locations for a Spee center (91) and a posterior movement axis (92) which are constitutional elements in a person, and positions being drawn and paired on both side portions of said plate; an incisor guiding plate (56) provided with an inverted slant conical surface to map the forward, backward, left, and right intercuspal inclinations for reproducing jaw movements in a person toward forward, backward, left, and right so that the tip of an incisor guiding pin (54) is slid along said slant surface; and a conversion plate (1) mounted to a base of a lower jaw frame (52) together with a lower jaw plaster dentition model [(52)] (7) for operating and reproducing physiological states for the intercuspal position and the posterior occlusal position in a person.

Figure 4:
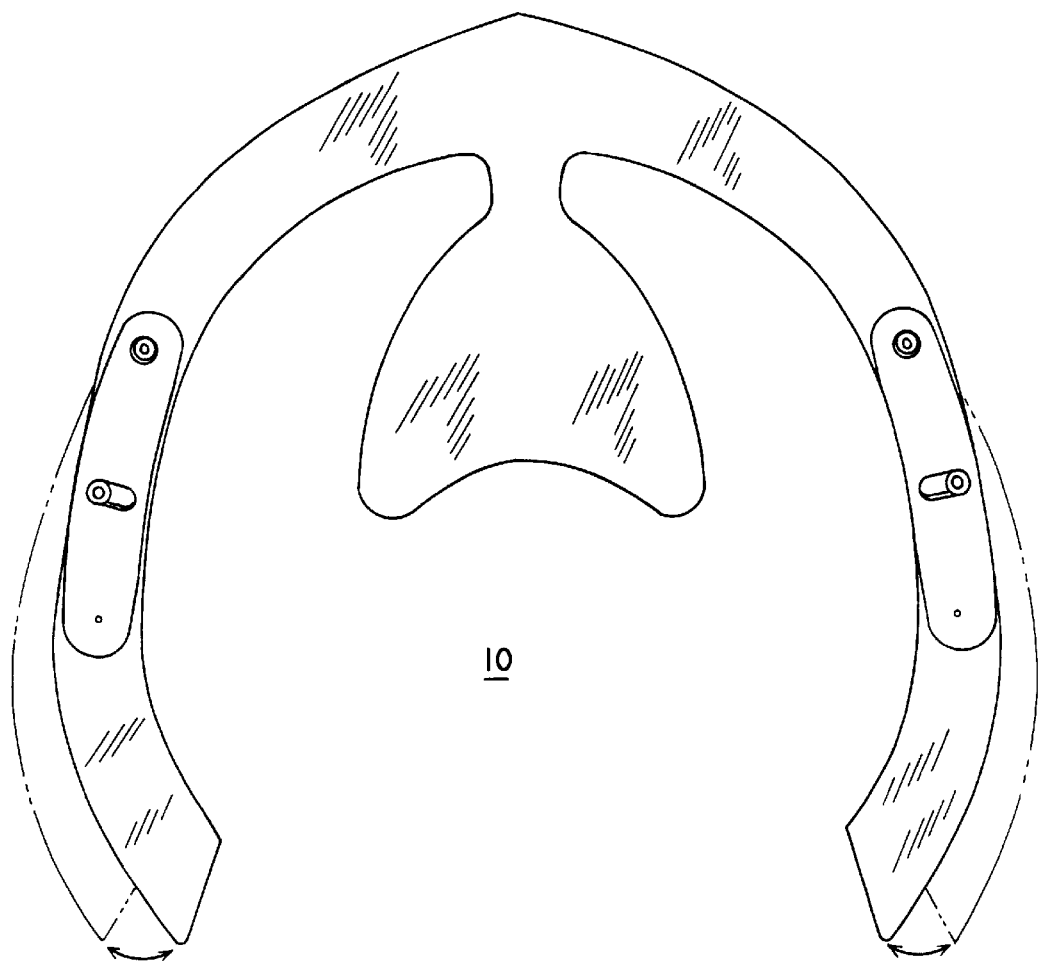
FIG. 4 is a plan view of a Camper face bow.
Figure 5A:
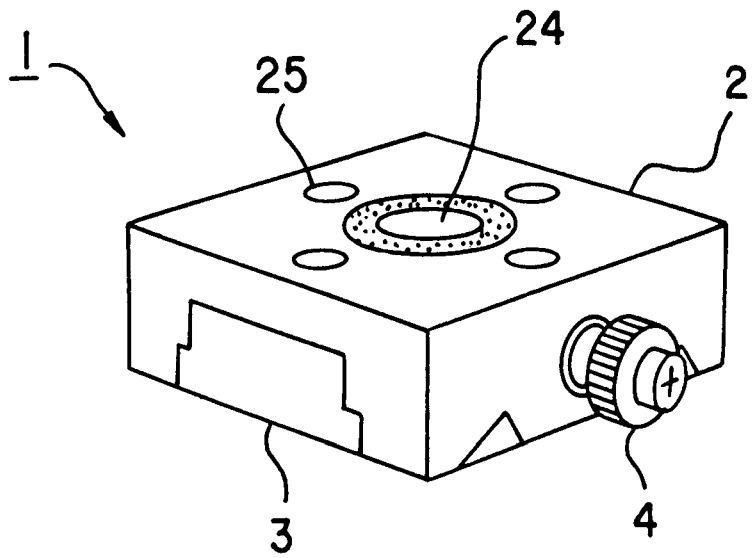
FIGS. 5a and 5b are perspective views of a conversion plate at binding states of engagement fixing and slide fixing respectively.
Figure 5B:
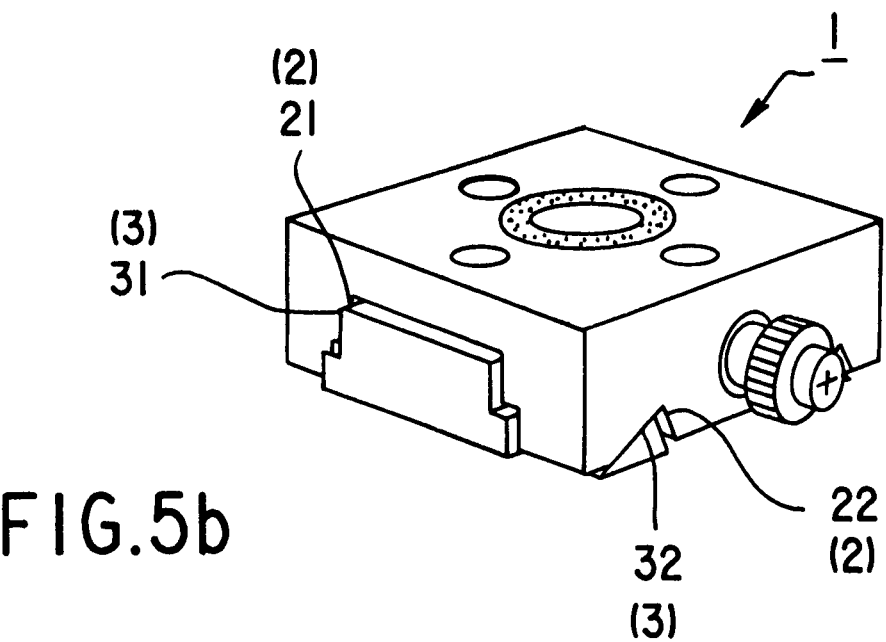

The articulator also is provided with a Camper face bow (10), as an accessory part, for recording the Camper plane which is parallel with the occlusal plane in a person. FIG. 4 shows a plan view of a Camper face bow. This Camper face bow (10) is to view (record) the left and right symmetry of the upper jaw occlusal plane, and holds mastoid processes on the left and right in a person with both ends of the bow.

In the articulator (5), the occlusal plane table (8) has a forward inclination of 10 degree and is used to mount the upper jaw dentition plaster model (6) (hereinafter called the upper jaw model) to the upper jaw frame (51) using a silicon core (putty) for the upper jaw occlusal plane established with respect to the reference Camper plane (prosthetics plane) in a way corresponding to that for full denture prosthetics. To establish the reference for the upper jaw occlusal plane, the Camper face bow is used.

In this case, the upper jaw incisor point (U1) is established at the location which is equally apart by 10 cm from the condyle ball on each side and corresponds to the vertex of the Bonwill triangle. Subsequently, the lower jaw dentition plaster model (7) is mounted with respect to the upper jaw model, keeping the centric relation (anterior superior position).

The occlusal analysis plate (9) is placed on and fixed to the top face (above the upper jaw frame) of the articulator (5) and has on both right and left sides thereof four (namely, 4 pairs) transparent small holes (sketched points) indicating the Spee centers (91). When the most anterior Spee center (91) is used, the tail of the Spee curve will rise and when the most posterior one is used, the tail will fall. Of these four pairs, the one most suitable to the relevant individual should be used. The occlusal analysis plate (9) also has on both the left and right sides thereof three (namely, 3 pairs) small holes (sketched points) indicating the posterior movement axes (Retrop. A) (92) for establishing the posterior guiding angle (degrees). When the most posterior movement axis (92) is used, the posterior guiding angle will be steep and when the most anterior one is used, the angle will be gentle. These should be used as a set together with one of the three kinds of incisor guiding plates (56) described below.

Three kinds of incisor guiding plates (56) are prepared, each being shaped in cone with a different development angle and paired with a corresponding posterior movement axis (92) for use. For a typical dentition occlusion with normal temporomandibular joint, use a posterior movement angle of 30 degrees and a development angle of 100 degrees. For full denture prosthetics, use a posterior movement angle of 15 degrees and a development angle of 140 degrees. For a moderate occlusal dentition between the above two, use a posterior movement angle of 22 degrees and a development angle of 120 degrees. (not illustrated)

Since this incisor guiding plate (56) can accommodate movement of an incisor guide pin (54) forward, backward, left, and right and can measure each inclination, the plate not only guides incisors as previously but also guides molars (works as a molar guiding pin).

The conversion plate (1) is characterized in that a main body of said conversion plate is divided into an upper structural member (2) and a lower structural member (3), binding surfaces of both members (2, 3) are formed to rise and fall so that the surfaces can be fitted or engaged with each other by male and female elements and can slide in the direction parallel with the Condyle path angle ($\theta$=30 degrees), and an occlusual state is relatively converted between said conversion plate and an upper jaw dentition plaster model (6) mounted onto an upper jaw frame (51) of said dental articulatory (5), by sliding on said binding surfaces said upper structural member (2) with said lower jaw dentition plaster model (7) mounted so that physiological occlusion state related to intercuspal position (by engagement fixing) and posterior occlusal position (by slide fixing) can be operated and reproduced.

Regarding the temporomandibular joint function, the upper surface of the Fossa box at the temporomandibular joint area of the articulator (5) performs the load receiving function and the lower surface of that performs the tractive function.

Thus, in an articulator (5) with the distance between the upper and lower jaw frames (51, 52) set to 10 cm (equal to the length of a side of Bonwill's triangle), when the angle of the occlusal plane with respect to the FH plane (horizontal plane) is set to 10 degrees as the same in a person, the Balkwill angle on the articulator (5) becomes about 25 degrees as the same in a person.

Further, since the posterior condyle path angle in a person is about 28.5 degrees in a backward and upward direction from he FH plane [Hiroaki Kawabata, Study on various condyle positions on a sagittal plane-especially on stabilized condyle position, Journal of Japanese Prosthetics Dentistry Academy, pp. 403–429, 1971], the condyle path angle ($\theta=30$ degrees) can be used which a common articulator with an average value employs.

Furthermore, in an articulator with a distance of 10 cm between the upper and lower jaw frames (51, 52) and an incisor guiding pin (54) located forward by 11 cm, if the posterior guiding angle of the incisor guiding plate (56) is set to 30 degrees for the case of a 30 degree posterior condyle path angle, the posterior incisor path angle will be the same as in a person, 26 degrees [Shoji Kono, Analysis of posterior movement from the intercuspal position to the posterior dentition contact position, Journal of Japanese Prosthetics Dentistry Academy No. 15, pp. 200–209, 1974]. At this time, if the posterior guiding angle and the posterior condyle path angle of the incisor guiding plate (56) are established, then the rotational center (92) of the lower jaw frame (52) (posterior movement axis) can be established.

Further, a Spee curve is drawn with its focal point at the Spee center (apex of the oral cavity cone) (91) in a person, and then the posterior guiding surface angle based on the lower molar buccal cusp, and the lingual cusp mesial slant surface angle based on upper molar mesial fossa, can respectively be determined, with respect to the arc with its focal point at the posterior movement axes (92).

Firstly, a conversion plate (1) mounted onto the occlusal articulator (5) will be described.

As can be seen from FIGS. 5 to 8, a main body of the conversion plate (1) is divided into an upper structural member (2) and a lower structural member (3).

Figure 6:
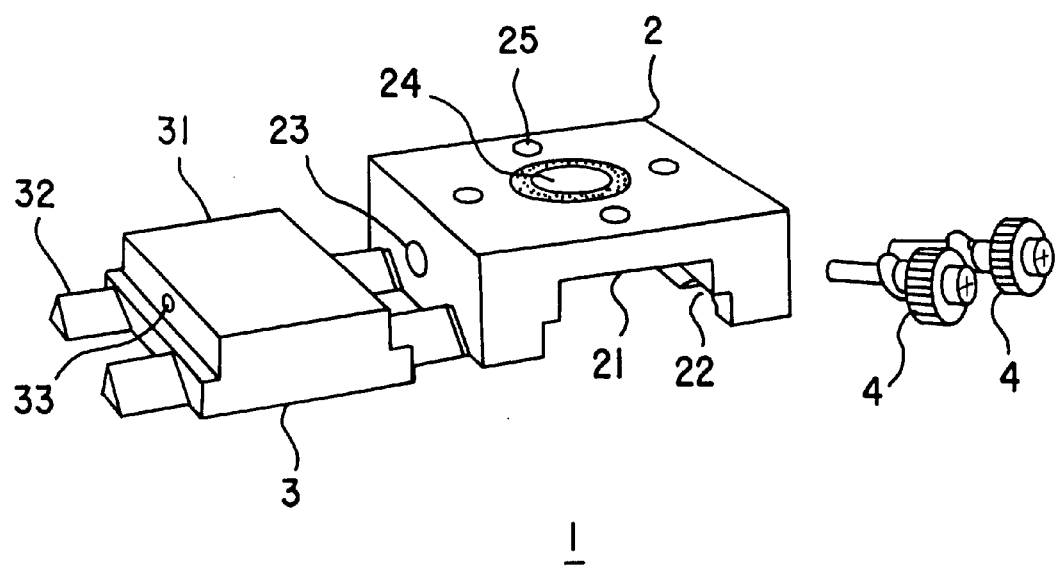
FIG. 6 is an assembly view of structural elements of a conversion plate.
Figure 7A:
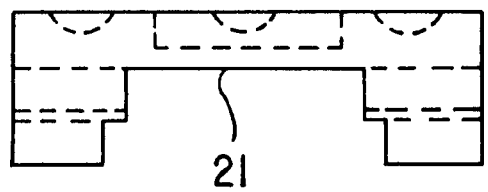
FIGS. 7a, 7b and 7c are front, left-side, and plan views of an upper structural member respectively.
Figure 7B:
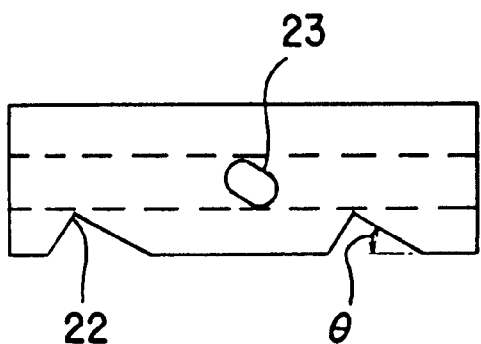
Figure 7C:
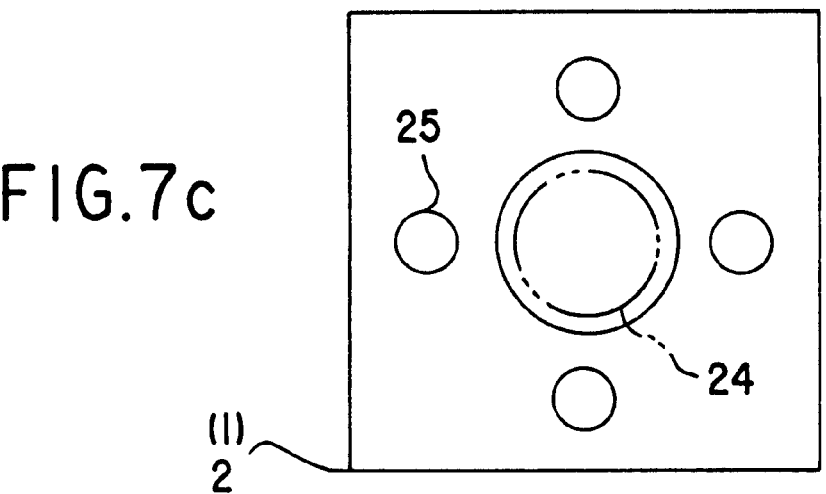

As shown in FIGS. 6 and 7, the upper structural member (2) has at the bottom face thereof a recess (21) formed in a groove (a protuberance in the front view), and has at two locations thereof notched surfaces extending from a side portion at the bottom thereof to the side face thereof, namely two triangular elements (female) (22). This triangular element (22) is a right triangle with two interior angles of 30 degrees and 60 degrees other than the right angle. The member (2) has at the central portion of a side face thereof an oblong hole (23) penetrating through the recessed portion (21). Further, the member (2) has on the top face thereof a permanent magnet (24), which is embedded at the center of the top face but some surface of which is exposed free, and has four circular cavities (25) arranged at four locations which are equally distant from the center and equally spaced in the circumferential direction. This permanent magnet (24) and cavities (25) are used to locate and fix the lower jaw dentition plaster model (7). The right and left portions of the member (2) are symmetric with respect to the center line in the front view.

Figure 8A:
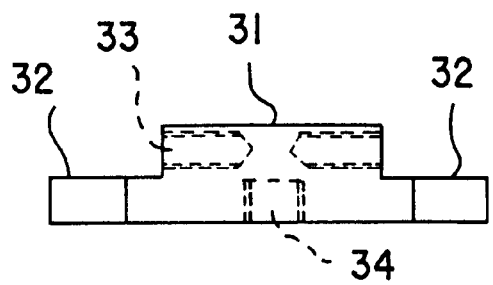
FIGS. 8a, 8b and 8c are front, left-side, and bottom views of a lower structural member respectively.
Figure 8B:
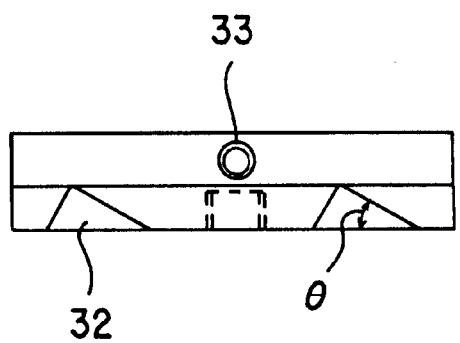
Figure 8C:
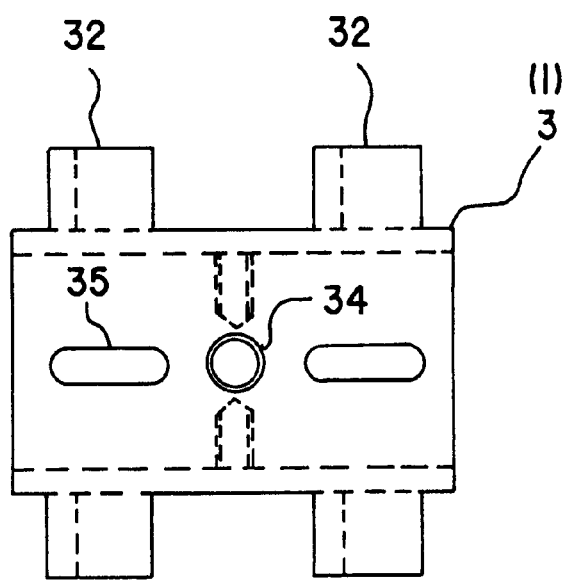

As shown in FIGS. 6 and 8, the lower structural member (3) has a protuberance (31) formed as a rail at the top face thereof (protuberance in the front view), and has at two locations on a side face thereof two triangular elements (male) (32) protruding outward (formed in brackets). Each triangular element (32) is a right triangle with two interior angles of 30 degrees and 60 degrees other than the right angle. The member (3) has at the upper central portion of a side face thereof a threaded hole (33). The member (3) has at the central portion of the bottom face thereof a threaded hole (34) for fixing the lower jaw frame, and has oblong cavities (35) at forward and backward points on the center line. These threaded holes (34) and cavity (35) are used to fix the member (3) to the lower jaw frame (52). The right and left portions of the member (2) are symmetric with respect to the center line in the front view.

Thus, binding surfaces of the upper structural member (2) and the lower structural member (3) are well-arranged surfaces formed to rise and fall, and can fit or engage with each other through the male and female elements (21, 31; 22, 32) when mounted onto the lower jaw frame (51) of the articulatory (5) and can also slide parallel with each other in the direction of condole path angle (0). The binding surface for the engagement, as described above, is formed to include the two sides of a right triangle with two interior angles of 30 degrees and 60 degrees other than a right angle, and both members (2, 3) have such a binding relationship in which both members can slide (be operated to shift) relatively to each other in a forward and downward direction (backward and upward of 30 degrees (conforming to the condole path angle $\theta$) in the mounted elevation view. For the engagement fixing and slide fixing, a screw (4, 4), inserted into the oblong hole (23) on the upper structural member (2) and the threaded hole (33) on the lower structural member (3) on each side on the right and left, is tightened and fixed. The "relatively" will later be described in detail.

A procedure for operating the articulator (5) is as follows.

Figure 9:
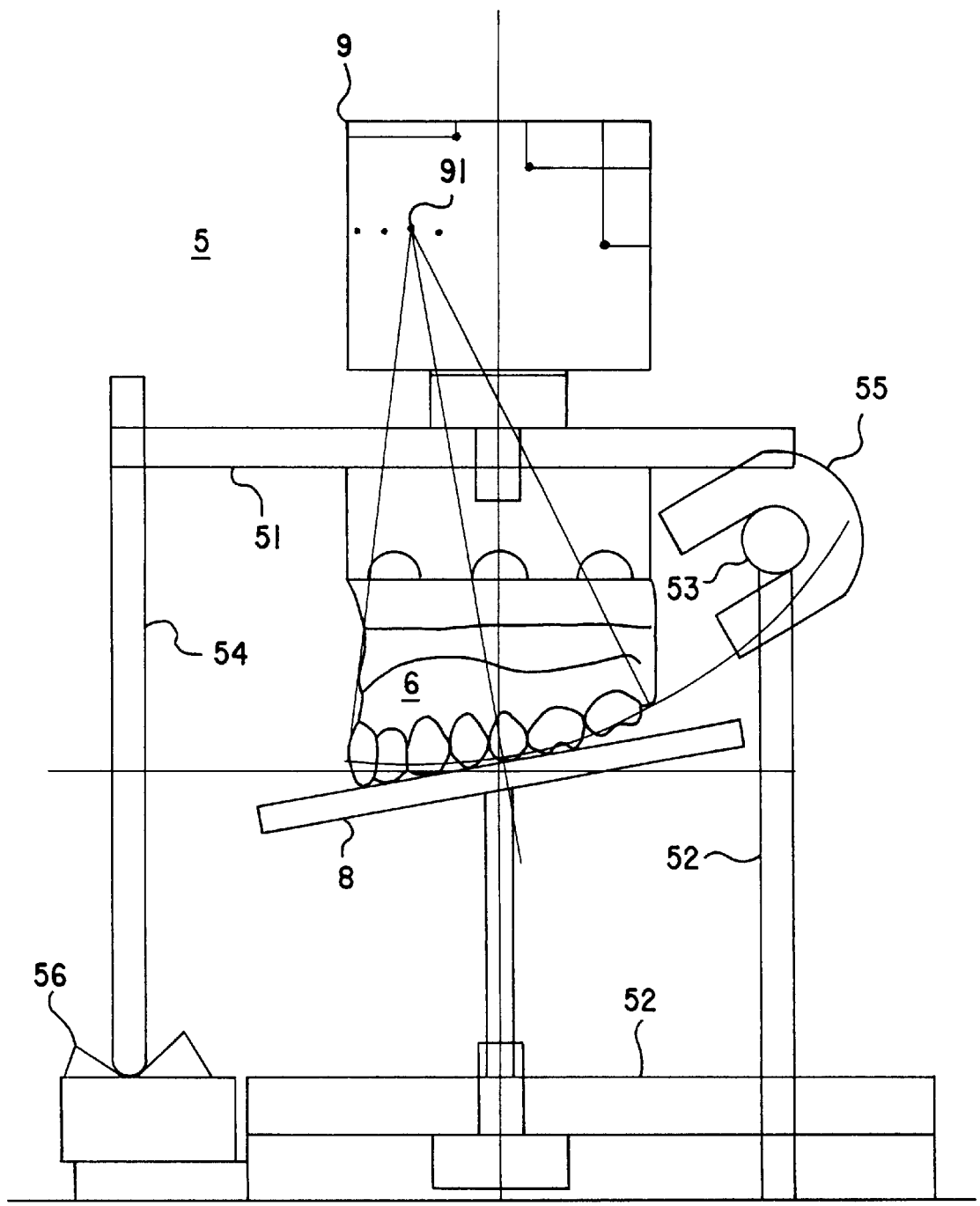
FIG. 9 is a side view showing how to mount a dentition plaster model of an upper jar.

As shown in FIG. 9 illustrating how the upper jaw dentition plaster model (6) (hereafter referred to as upper jaw model) is mounted using the occlusal plant table (8), the occlusal plane table (8) with the lower jaw frame (52) as a base is mounted to the articulator (5), a mold of the upper jaw dentition is modeled using a Camper face bow (10) (refer to FIG. 4) loaded with a silicon core (putty) (not illustrated) (the Camper plane is recorded), then the silicon core (putty) (not illustrated) is transferred from the Camper face bow (10) onto the occlusal plane table (8),and the upper jaw model is mounted onto the upper jaw frame (51), lining up the median line with the U1 (incisor). At this time, the condyle path angle should be set to 30 degrees.

Figure 10:
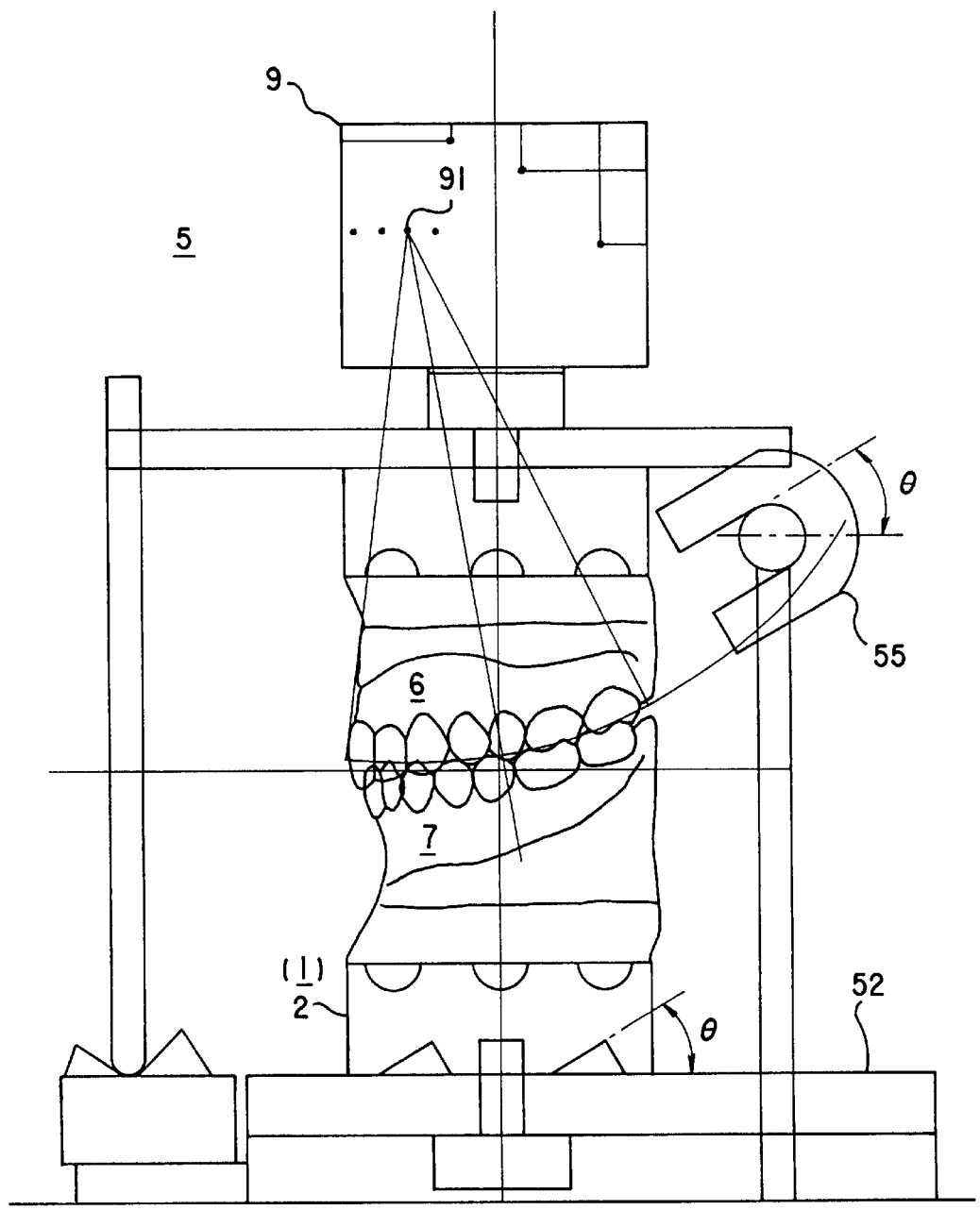
FIG. 10 is a side view showing how to mount a conversion plate and a dentition plaster model of a lower jaw.

As shown in FIG. 10 illustrating how the lower jaw dentition plaster model (thereafter referred to as the lower jaw model) (7) and the converter plate (1) are mounted, the silicon core (putty) (not illustrated) and the occlusal plane table (8) are removed from the articulatory (5), the engagement-fixed converter plate (1) is mounted using the lower jaw frame (52) of the articulator (5) as a base, the lower jaw model (7) is mounted to the upper structural member (2), and thus the occlusal state related to the intercuspal position is reproduced between the upper jaw model (6) and the conversion plate.

Figure 11:
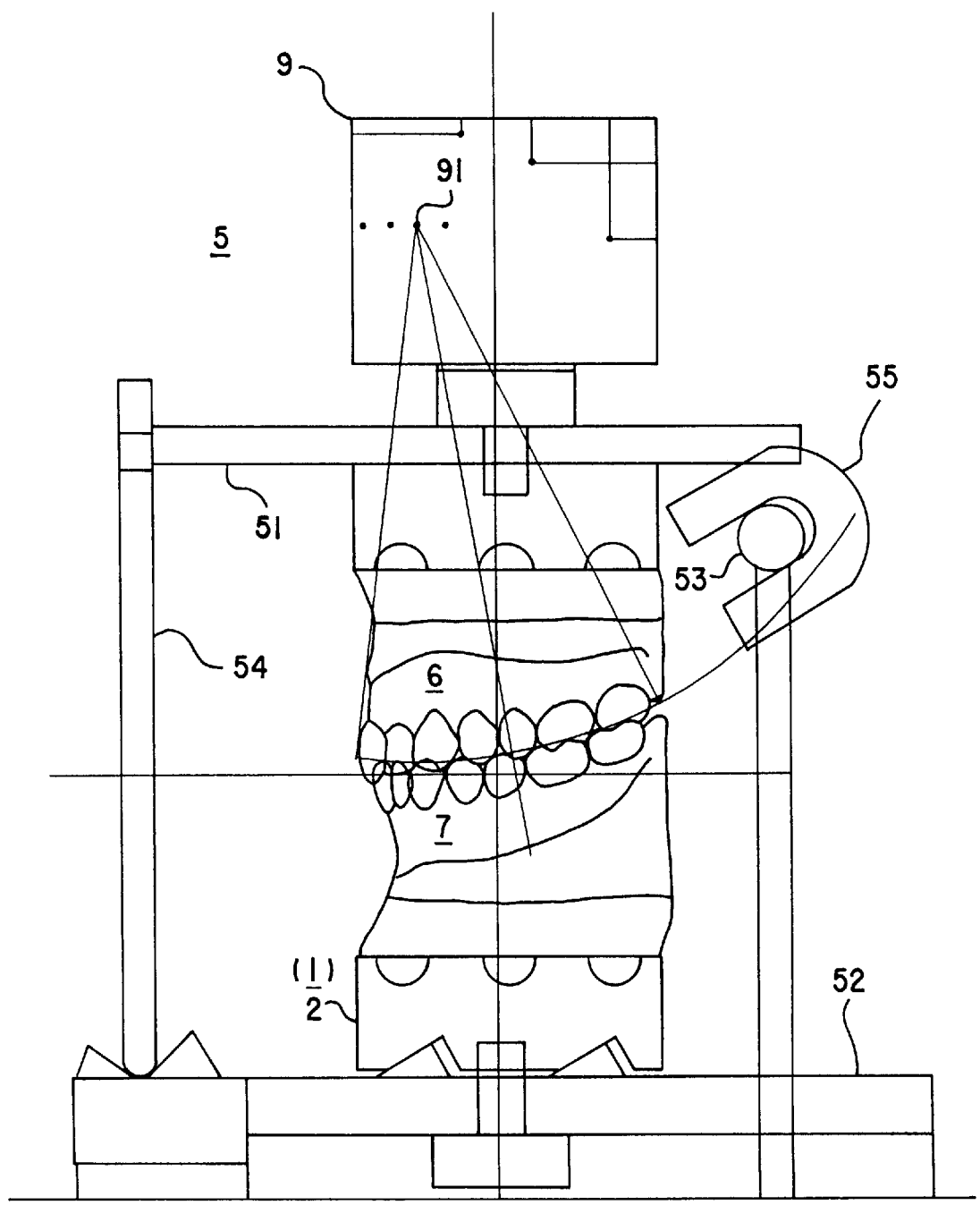
FIG. 11 is a side view showing how to operate for reproducing the physiological occulsal state related to the intercuspal position with the lower jaw mobility taken into account.

As in FIG. 11 illustrating the operation for reproducing the physiological occlusion state related to the intercuspal position with the lower jaw mobility taken into account, the upper jaw model (6) is set to a free state (non-binding), the upper structural member (2) of the converter plate (1) is set to slide fixing, a state is created where the lower jaw can slide relatively to the upper jaw and parallel in a forward and downward direction of 30 degrees, and thus the physiologic occlusion state related to the intercuspal position is reproduced. During this time, the displacement (slip) between the condyle ball (53) and the incisor guiding pin (54) should be noted.

Figure 12:
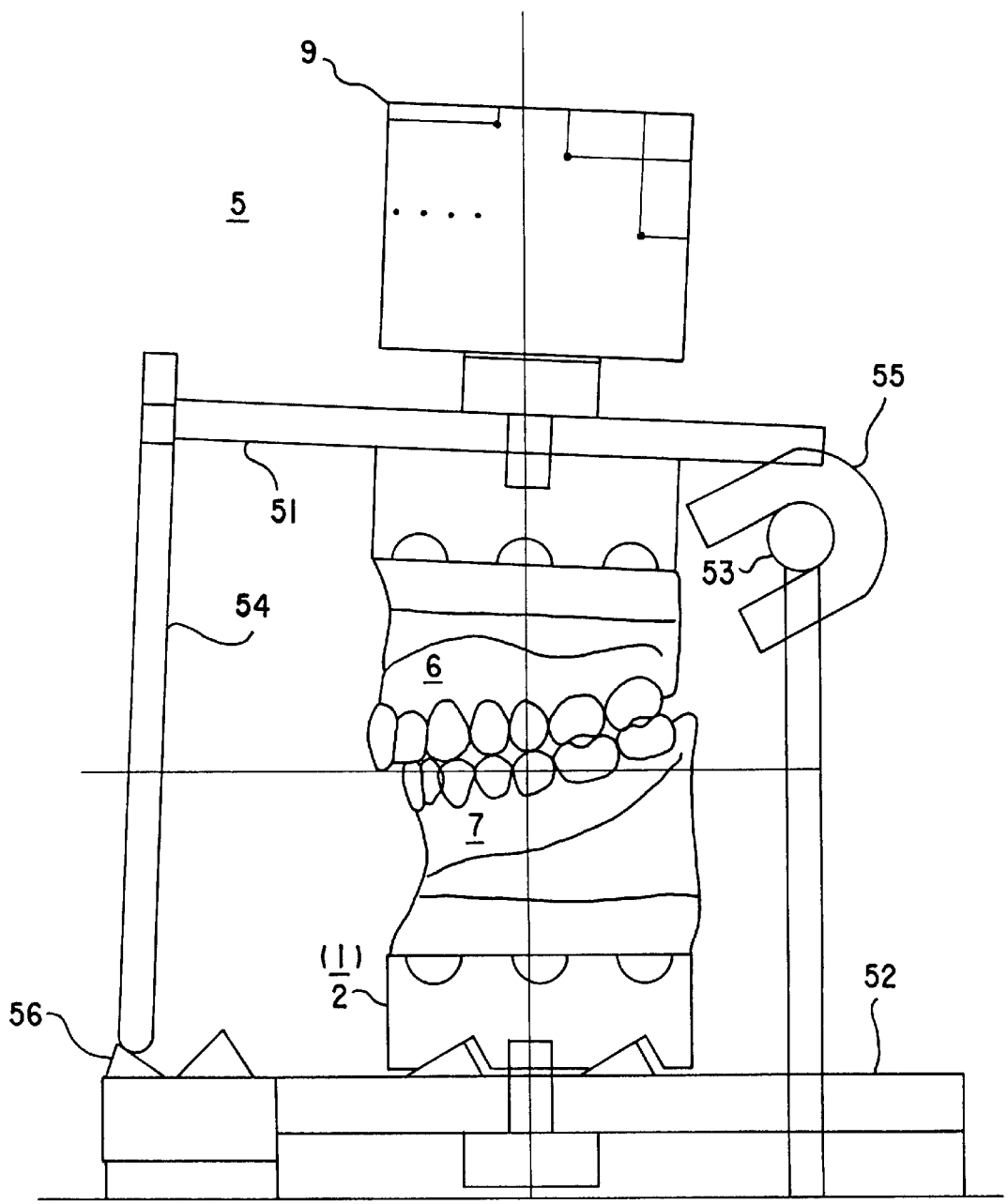
FIG. 12 is a side view showing how to operate for reproducing the physiological occulsal state related to the posterior occlusal position with the lower jaw mobility taken into account.

As shown in FIG. 12 illustrating the operation for reproducing the physiological occlusion state related to the posterior occlusal position with the lower jaw mobility taken into account, the upper frame (51) and the upper jaw model (6) are moved forward from intercuspal position shown in FIG. 11 so that the joint area (55) of the upper jaw frame (51) is brought into contact with the condyle ball (53) (hereinafter referred to as upper jaw shift),and thus the physiologic occlusion state related to the posterior occlusal position is reproduced. During this time, the displacement (slip) between the condyle ball (53) and the incisor guiding pin (54) should be noted.

Figure 13:
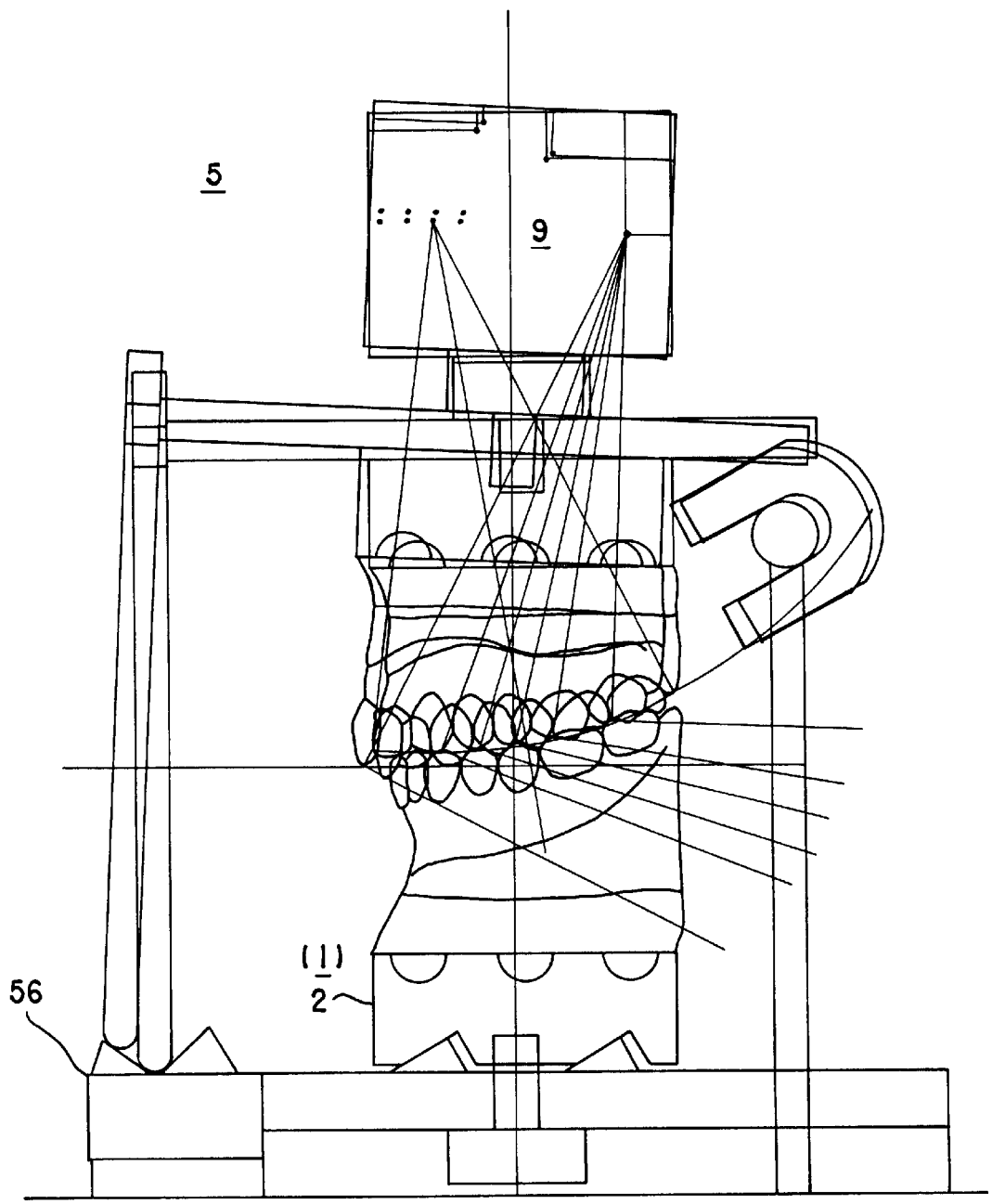
FIG. 13 is a side view showing a physiological occulsal state in which the physiological occulsal states of FIG. 11 and FIG. 12 are combined.
Figure 14:
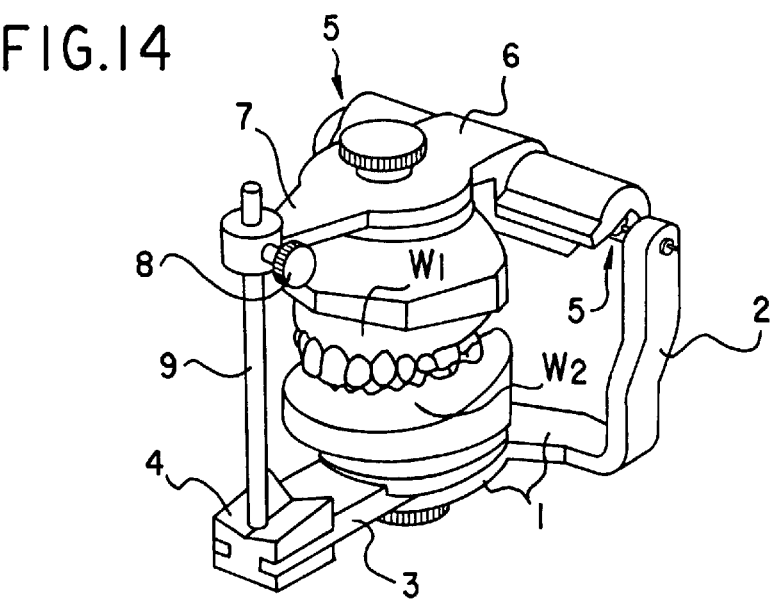
FIG. 14 is a perspective view of an example of a conventional articulator.
Figure 15:
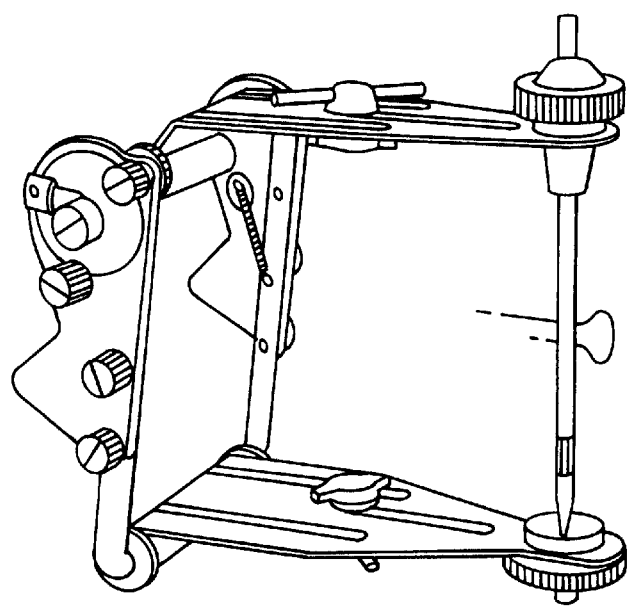
FIG. 15 is a view showing a Gerber's articulator (reproduced from a catalogue).

As shown in FIG. 13 illustrating a composite diagram of the physiologic occlusion states of FIGS. 11 and 12, the Physiological occlusion states related to the intercuspal position and the posterior occlusal position are reproduced by the upper jaw shift operation. Thus, in the articulator (5) with a condyle path angle (θ) set to 30 degrees, the converter plate (1) is mounted to the lower jaw frame (52) as a base, the upper structural member (2) with the lower jaw model (7) mounted is slid over the binding surface and the upper jaw shift is, operated, and thereby the occlusal state is relatively converted between the upper jaw model mounted onto the upper jaw frame (51) of the articulator (5) and the lower jaw model, and physiologic occlusal states related to the intercuspal position and the posterior occlusal position can be operated and reproduced.

"Relatively", here, means that since the upper jaw is considered to be fixed when the occlusion states in a person is modeled, the upper jaw shift operation described above has taken into the mobility of the lower jaw . Therefore, for operating and reproducing the physiological occlusion states using. an articulator (5), even if the operation of the member is performed only in form of the upper jaw shift, it is important and necessary to interpret the shift amount as the displacement of the lower jaw with respect to the upper jaw and to obtain the characteristics of the positional relationship between the upper and lower jaws (reproduction of physiological occlusion states).

As described above, an articulator of the present invention makes it possible, mainly through the shift operation of the conversion plate, to reproduce jaw movement as accurately as that in a person, and thereby makes it possible to reproduce or analyze the physiological occlusal state related to the posterior occlusal position, which has been impossible either to reproduce or to analyze in the conventional articulator. In addition, a conversion plate of the present invention, when incorporated to be reassembled as a part into a conventional articulator which has been in advance disassembled, allows said conventional articulator to be converted into the one having the similar function as that of the present invention. Further the conversion plate may be distributed as a single accessory part and therefore its widespread can be expected because the part is inexpensive and is adapted to mass production.

What is claimed is:

1. A dental articulator for use with a dentition plaster model installed between upper and lower jaw frames during the treatment of occlusion of upper an lower dentitions of a patient and during the creation of prosthetics for reproducing an occlusal state, said dental articulator comprising:

an occlusal plane table for vertically supporting said upper detention and having a slanted table surface with a forward inclination corresponding substantially to that of an occlusal plane in the patient;

an occlusion analysis plate movably supported by the upper jaw frame and having a plurality of averaged positions established at multiple locations for determining a Spee center and a posterior movement axis which are constitutional elements in the patient, said averaged positions being drawn and paired on both side portions of said plate;

an incisor guiding plate having opposed slanted surfaces to map the forward, backward, left, and right intercuspal inclinations for reproducing jaw movements in the patient forwardly, backwardly, left and right, and an incisor guiding pin having a tip adapted to slide along said slanted surfaces of incisor guiding plate;

a conversion plate mounted to a base formed by the lower jaw frame, together with a lower jaw plaster dentition model mounted thereon for operating and reproducing physiological states for the intercuspal positions and the posterior occlusal positions of said patient; and said incisor guiding pin cooperating with said incisor guiding plate, wherein a physiological occlusion state is reproduced for analysis by allowing a load receiving function and a tractive function to operate in all the directions of movement which correspond to those of the temporomandibular joint function in said patient.

2. A dental articulator in accordance with claim 1, including a Camper face bow capable of disposition on said occlusal plane table as an accessory part for recording a Camper plane in parallel with said occlusal plane in said patient; and means for mounting said Camper face bow to said occlusal plane table.

3. A dental articulator in accordance with claim 1, wherein said conversion plate has a body divided into an upper structural member and a lower structural member, binding surfaces of both members being formed with surface protrusions adapted to effect a rise and fall of said upper structural member with respect to said lower structural member so that the surfaces can be fitted or engaged with each other by male and female elements and can slide in a sliding direction parrallel with a Condyle path angle, and both said members are provided on the left and right side faces thereof with either a threaded hole or an oblong hole for a temporary fixing together by a screw, and an occlusal state is relatively converted between said conversion plate and an upper jaw dentition plaster model mounted onto an upper jaw frame of said dental articulator, by sliding on said binding surfaces said upper structural member with said lower jaw dentition plaster model mounted thereon so that physiological occlusion states related to said intercuspal positions and said posterior occlusal positions can be operated and reproduced.

4. A dental ariticulator in accordance with claim 3, wherein said male and female elements include means forming recess and protuberance members formed as triangular elements, said binding surfaces being fit with each other by cooperation of said recess and said projection members and engaged with each other by said triangular elements, said binding surfaces for engagement being formed to include two sides thereof intersecting at a right angle with two interior angles of about 30 degrees and about 60 degrees, other than the right angle so that the inclination in said sliding direction and the Condyle path angle are the same.

5. A conversion plate in a dental articulator for use during treatment of occlusion of upper and lower dentitions and during creation of prosthetics, including a lower jaw frame forming a base, means for mounting a dentition plaster model onto said dental articulator whose Condyle path angle has been set to 30 degrees, wherein a main body of a conversion plate supported by said lower jaw frame is divided into an upper structural member and lower structural member, cooperating binding surfaces formed on both of said structural members to effect rising and falling between structural members so that the surfaces thereof can be fitted or engaged with each other by male and female elements which can slide in the direction parallel with Condyle path angle, said both members being provided on opposite side faces thereof with either a threaded hole or an oblong hole for temporary fixing together by a screw, and an occlusal state is relatively converted between said conversion plate and an upper jaw dentition plaster model mounted onto an upper jaw frame of said dental articulator, by sliding on said binding surfaces said upper structural member with said lower jaw detention plaster model mounted thereon so that physyiological occlusion states related to intercuspal positions and posterior occlusal positions can be operated and reproduced.

6. A conversion plate for a dental arcticulator in accordance with claim 5, wherein said male and female elements are each defined as a recess and a projection forming triangular elements, said binding surfaces being arranged to fit with each other by said recess and said projection and engage with each other by said triangular elements, and said binding surfaces related to said engagement being formed to include two sides of said recess and said projection intersecting in a right angle with two interior angles of 30 degrees and 60 degrees other than the right angle so that the inclination in said sliding direction and the Condyle path angle are the same.

* * * * *